(12) United States Patent
Krautkremer et al.

(10) Patent No.: US 10,130,497 B2
(45) Date of Patent: Nov. 20, 2018

(54) STENT WITH RETRACTABLE ANCHORS

(71) Applicant: BOSTON SCIENTIFIC SCIMED, INC., Maple Grove, MN (US)

(72) Inventors: Daniel L. Krautkremer, Plymouth, MN (US); Allison M. Pearlman, Holden, MA (US); Kathleen Corcoran, Watertown, MA (US); Jill M. White, Shakopee, MN (US); Kevin Walsh, Wellesly, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 67 days.

(21) Appl. No.: 15/047,024

(22) Filed: Feb. 18, 2016

(65) Prior Publication Data

US 2016/0242940 A1    Aug. 25, 2016

Related U.S. Application Data

(60) Provisional application No. 62/118,652, filed on Feb. 20, 2015.

(51) Int. Cl.
*A61F 2/848*    (2013.01)
*A61F 2/04*    (2013.01)
(Continued)

(52) U.S. Cl.
CPC ............... *A61F 2/848* (2013.01); *A61F 2/04* (2013.01); *A61F 2/06* (2013.01); *A61F 2/07* (2013.01); *A61F 2/90* (2013.01); *A61F 2002/043* (2013.01); *A61F 2002/044* (2013.01); *A61F 2002/046* (2013.01); *A61F 2002/047* (2013.01); *A61F 2002/048* (2013.01);
(Continued)

(58) Field of Classification Search
CPC ...... A61F 2002/044; A61F 2/82–2/945; A61F 2220/0008–2220/0016; A61F 2/04–2002/077; A61F 2/24–2/2475
See application file for complete search history.

(56) References Cited

U.S. PATENT DOCUMENTS 5,167,614 A    12/1992  Tessmann et al.
5,397,355 A    3/1995   Marin et al.
(Continued)

FOREIGN PATENT DOCUMENTS

EP    1923020 A2    5/2008
JP    2008-119480 A1    5/2008
(Continued)

*Primary Examiner* — Yashita Sharma
*Assistant Examiner* — Rebecca Preston
(74) *Attorney, Agent, or Firm* — Seager, Tufte & Wickhem, LLP

(57) ABSTRACT

A stent includes a tubular support structure extending from a distal end to a proximal end, the tubular support structure including an inner surface and an outer surface. A retractable anchor system is disposed relative to the tubular support structure and includes a frame member and a plurality of retractable anchors secured to the frame member. The plurality of retractable anchors are biased to a deployed configuration in which the plurality of retractable anchors extend radially outward from the outer surface of the tubular support structure but are radially inwardly compressible into a delivery configuration.

17 Claims, 11 Drawing Sheets

(51) Int. Cl.
*A61F 2/06* (2013.01)
*A61F 2/90* (2013.01)
*A61F 2/07* (2013.01)
*A61F 2/82* (2013.01)

(52) U.S. Cl.
CPC . *A61F 2002/826* (2013.01); *A61F 2002/8483* (2013.01); *A61F 2002/8486* (2013.01); *A61F 2210/0004* (2013.01); *A61F 2210/0014* (2013.01); *A61F 2220/0016* (2013.01); *A61F 2220/0025* (2013.01); *A61F 2250/0008* (2013.01); *A61F 2250/0059* (2013.01); *A61F 2250/0065* (2013.01); *A61F 2250/0067* (2013.01)

(56) References Cited

U.S. PATENT DOCUMENTS

| | | | |
|---|---|---|---|
| 6,911,042 B2 | 6/2005 | Weadock | |
| 7,223,284 B2 | 5/2007 | Khosravi et al. | |
| 7,655,034 B2 | 2/2010 | Mitchell et al. | |
| 7,867,267 B2 | 1/2011 | Sullivan et al. | |
| 7,905,915 B2 | 3/2011 | Young et al. | |
| 7,914,568 B2 | 3/2011 | Cully et al. | |
| 8,348,988 B2 | 1/2013 | Lad et al. | |
| 8,372,141 B2 | 2/2013 | Majercak et al. | |
| 8,372,142 B2 | 2/2013 | Majercak et al. | |
| 8,372,143 B2 | 2/2013 | Majercak et al. | |
| 8,394,139 B2 | 3/2013 | Roeder et al. | |
| 8,444,688 B2 | 5/2013 | Sherry | |
| 8,702,785 B2 | 4/2014 | Khan et al. | |
| 8,747,457 B2 | 6/2014 | Petersen | |
| 8,821,565 B2 | 9/2014 | Demetriades et al. | |
| 8,858,617 B2 | 10/2014 | Roeder et al. | |
| 8,864,813 B2 | 10/2014 | Barr | |
| 9,089,445 B2 | 7/2015 | Agnew et al. | |
| 9,192,466 B2 | 11/2015 | Kovalsky et al. | |
| 9,237,959 B2 | 1/2016 | Cage | |
| 2002/0032481 A1* | 3/2002 | Gabbay | A61F 2/2418 623/2.11 |
| 2005/0033398 A1* | 2/2005 | Seguin | A61B 17/072 623/1.11 |
| 2005/0143825 A1* | 6/2005 | Enayati | A61F 2/446 623/17.16 |
| 2007/0027526 A1 | 2/2007 | Demetriades et al. | |
| 2007/0027548 A1* | 2/2007 | Levine | A61B 17/0401 623/23.7 |
| 2007/0051377 A1* | 3/2007 | Douk | A61B 17/00234 128/897 |
| 2008/0114442 A1 | 5/2008 | Mitchell et al. | |
| 2009/0048664 A1 | 2/2009 | Cage | |
| 2009/0082847 A1 | 3/2009 | Zacharias | |
| 2009/0270967 A1 | 10/2009 | Flemming, III et al. | |
| 2010/0256725 A1 | 10/2010 | Rasmussen | |
| 2012/0130470 A1 | 5/2012 | Agnew et al. | |
| 2012/0232637 A1 | 9/2012 | Demetriades et al. | |
| 2013/0018452 A1* | 1/2013 | Weitzner | A61F 2/848 623/1.15 |
| 2013/0144375 A1 | 6/2013 | Giasolli et al. | |
| 2013/0172983 A1 | 7/2013 | Clerc et al. | |
| 2013/0245749 A1 | 9/2013 | Sherry | |
| 2014/0067038 A1 | 3/2014 | Daugherty et al. | |
| 2014/0081416 A1 | 3/2014 | Clerc et al. | |
| 2014/0277442 A1 | 9/2014 | Seddon et al. | |
| 2015/0119974 A1 | 4/2015 | Rothstein | |
| 2016/0074041 A1* | 3/2016 | Wirtel, III | A61B 17/0643 606/153 |
| 2016/0095725 A1 | 4/2016 | Roeder et al. | |

FOREIGN PATENT DOCUMENTS

| | | |
|---|---|---|
| JP | 2009-502343 A1 | 1/2009 |
| JP | 2012-152576 A1 | 8/2012 |
| WO | 2007016166 A2 | 2/2007 |
| WO | 2009042789 A2 | 4/2009 |

\* cited by examiner

STENT WITH RETRACTABLE ANCHORS

CROSS-REFERENCE TO RELATED APPLICATIONS

This application claims priority under 35 U.S.C. § 119(e) to U.S. Provisional Application No. 62/118,652, filed Feb. 20, 2015, the entire disclosure of which is herein incorporated by reference.

TECHNICAL FIELD

The disclosure is directed to an endoprosthesis, such as a stent. More particularly, the disclosure is directed to a stent including one or more anti-migration features.

BACKGROUND

An endoprosthesis may be configured to be positioned in a body lumen for a variety of medical applications. For example, an endoprosthesis may be used to treat a stenosis in a blood vessel, used to maintain a fluid opening or pathway in the vascular, urinary, biliary, tracheobronchial, esophageal or renal tracts, or to position a device such as an artificial valve or filter within a body lumen, in some instances. A variety of different stents have been developed, and may be manufactured by any one of a variety of different manufacturing methods and may be used according to any one of a variety of methods.

BRIEF SUMMARY

The disclosure provides design, material, manufacturing method, and use alternatives for stents. An example stent is disclosed. The stent comprises:
  a tubular support structure extending from a distal end to a proximal end, the tubular support structure including an inner surface and an outer surface; and
  a retractable anchor system disposed relative to the tubular support structure, the retractable anchor system including a frame member and a plurality of retractable anchors secured to the frame member;
  wherein the plurality of retractable anchors are biased to a deployed configuration in which the plurality of retractable anchors extend radially outward from the outer surface of the tubular support structure but are radially inwardly compressible into a delivery configuration.

Alternatively or additionally to any of the embodiments above, the retractable anchor system is biased into the deployed configuration.

Alternatively or additionally to any of the embodiments above, the plurality of retractable anchors are configured such that when the stent is implanted, the plurality of retractable anchors are pointed in a first direction to resist movement of the stent in the first direction.

Alternatively or additionally to any of the embodiments above, the frame member is woven into the tubular support structure such that the retractable anchor system may move axially relative to the tubular support structure.

Alternatively or additionally to any of the embodiments above, the retractable anchor system includes a retraction member at the proximal end of the stent, such that a proximal force applied to the retraction member causes the retractable anchor system to move proximally relative to the tubular support structure such that at least some of the retractable anchors are deflected radially inwardly via contact with a portion of the tubular support structure for subsequent removal of the stent.

Alternatively or additionally to any of the embodiments above, the retractable anchor system further comprises one or more additional frame members, each of which include a plurality of retractable anchors.

Alternatively or additionally to any of the embodiments above, each of the frame members are joined to a ring disposed at a proximal end of the retractable anchor system.

Alternatively or additionally to any of the embodiments above, wherein the retractable anchor system is disposed adjacent the inner surface of the tubular support structure.

Alternatively or additionally to any of the embodiments above, wherein the retractable anchor system is disposed adjacent the outer surface of the tubular support structure.

Alternatively or additionally to any of the embodiments above, wherein the tubular support structure is self-expanding.

Alternatively or additionally to any of the embodiments above, the tubular support structure comprises a braided support structure and the stent further comprises a polymeric covering disposed on the braided support structure; and the retractable anchor system further includes a ring disposed at an end of the retractable anchor system and the frame member further comprises a plurality of frame members extending from the ring and through the braided support structure.

Alternatively or additionally to any of the embodiments above, the braided support structure is self-expanding.

Alternatively or additionally to any of the embodiments above, wherein the retractable anchor system comprises a shape memory material.

Alternatively or additionally to any of the embodiments above, wherein the plurality of retractable anchors are configured such that when the stent is implanted in an esophagus, the plurality of retractable anchors are pointed in a first direction to resist downward movement of the stent in the first direction.

Alternatively or additionally to any of the embodiments above, wherein the retractable anchor system may move axially relative to the braided support structure.

Alternatively or additionally to any of the embodiments above, wherein the retractable anchor system includes a retraction member at the proximal end of the retractable anchor system, such that a proximal force applied to the hook causes the retractable anchor system to move proximally relative to the braided support structure such that at least some of the retractable anchors are deflected radially inwardly via contact with a portion of the braided support structure for subsequent removal of the stent.

A stent is disclosed. The stent comprises:
  a braided support structure extending from a distal end to a proximal end of the stent, the braided support structure including an inner surface and an outer surface;
  a polymeric covering disposed on the braided support structure; and
  a retractable anchor system including:
    a ring disposed at an end of the retractable anchor system;
    a plurality of frame members extending from the ring and through the braided support structure; and
    a plurality of retractable anchors secured to each of the plurality of frame members;
  wherein the plurality of retractable anchors are biased to a position in which the plurality of retractable anchors extend radially outward from the outer surface of the braided support structure.

Alternatively or additionally to any of the embodiments above, the braided support structure is self-expanding.

Alternatively or additionally to any of the embodiments above, the retractable anchor system comprises a shape memory material.

Alternatively or additionally to any of the embodiments above, the plurality of retractable anchors are configured such that when the esophageal stent is implanted, the plurality of retractable anchors are pointed in a first direction to resist downward movement of the stent in the first direction.

Alternatively or additionally to any of the embodiments above, the retractable anchor system may move axially relative to the braided support structure.

Alternatively or additionally to any of the embodiments above, the retractable anchor system includes a retraction member at the proximal end of the retractable anchor system, such that a proximal force applied to the hook causes the retractable anchor system to move proximally relative to the braided support structure such that at least some of the retractable anchors are deflected radially inwardly via contact with a portion of the braided support structure for subsequent removal of the esophageal stent.

A method for deploying a stent within a body lumen, such as for example a patient's esophagus, is disclosed. It will be appreciated that reference to a particular body lumen is intended as illustrative only, and is not intended to be limiting in any manner. In some cases, the stent includes a braided support structure and a retractable anchor system movable relative to the braided support structure, the retractable anchor system including a plurality of retractable anchors. The method comprises:

advancing the stent to a desired position within the body lumen in a radially compressed configuration; and expanding the stent to a radially expanded configuration;

wherein the plurality of retractable anchors of the retractable anchor system expand radially into an anchoring configuration in which the retractable anchors extend radially outward from the braided support member to engage a wall of the body lumen.

Alternatively or additionally to any of the embodiments above, wherein the retractable anchors extend in a first direction, once the stent has been deployed, in order to resist migration in the first direction.

Alternatively or additionally to any of the embodiments above, wherein the retractable anchor system is configured to be moved proximally relative to the braided support structure to move the retractable anchors in a radially inward direction for removal.

Alternatively or additionally to any of the embodiments above, wherein the braided support structure includes a stent removal loop configured to be moved proximally to cause the braided support structure to reduce in diameter for removal.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The aspects of the disclosure may be further understood in consideration of the following detailed description of various embodiments in connection with the accompanying drawings, in which.

Figure 1:
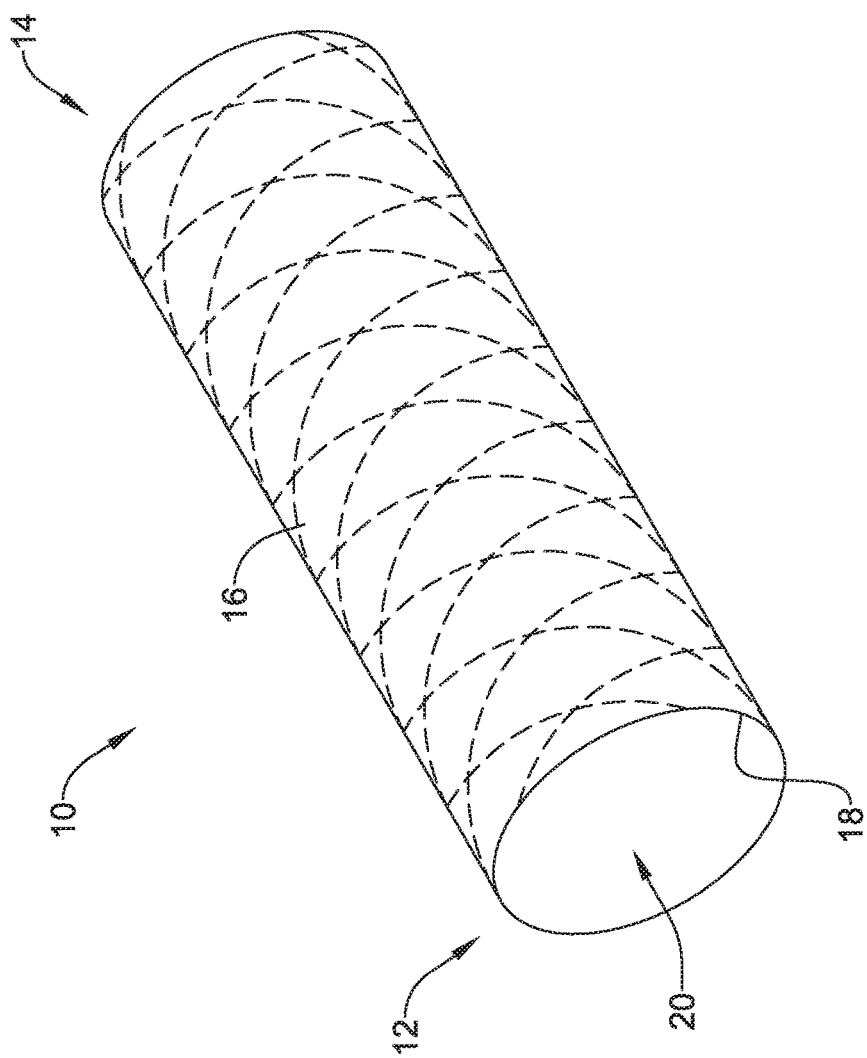
FIG. 1 is a perspective view of an illustrative stent in accordance with an embodiment of the disclosure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

FIG. 1 is a perspective view of an illustrative endoprosthesis 10. While the endoprosthesis 10 is described herein as being a stent 10 useful as an esophageal stent, it will be appreciated that various features of the stent 10, including its anti-migration features to be described herein, are applicable to any variety of different stents intended for deployment in a variety of different body systems and locations. The stent 10 extends from a proximal end 12 to a distal end 14 and includes an outer surface 16 and an inner surface 18 defining a lumen 20 extending through the stent 10. It will be appreciated that the terms distal and proximal are generally defined in terms of relative position within the body. Accordingly, it should be understood that references to distal and proximal in describing the stent 10 when not deployed are merely arbitrary, as the stent 10 could be used in any orientation. In some embodiments, the stent 10 may have a single layer construction, such as a braided stent, a knit stent or a laser cut stent or may have a multi-layer construction including a polymeric covering or sleeve covering the stent 10, for example disposed within or about, such as on an inner surface or an outer surface, at least a portion of the stent. In some cases, the construction details of the stent 10 may vary, depending on the intended use of the stent 10.

Figure 2:
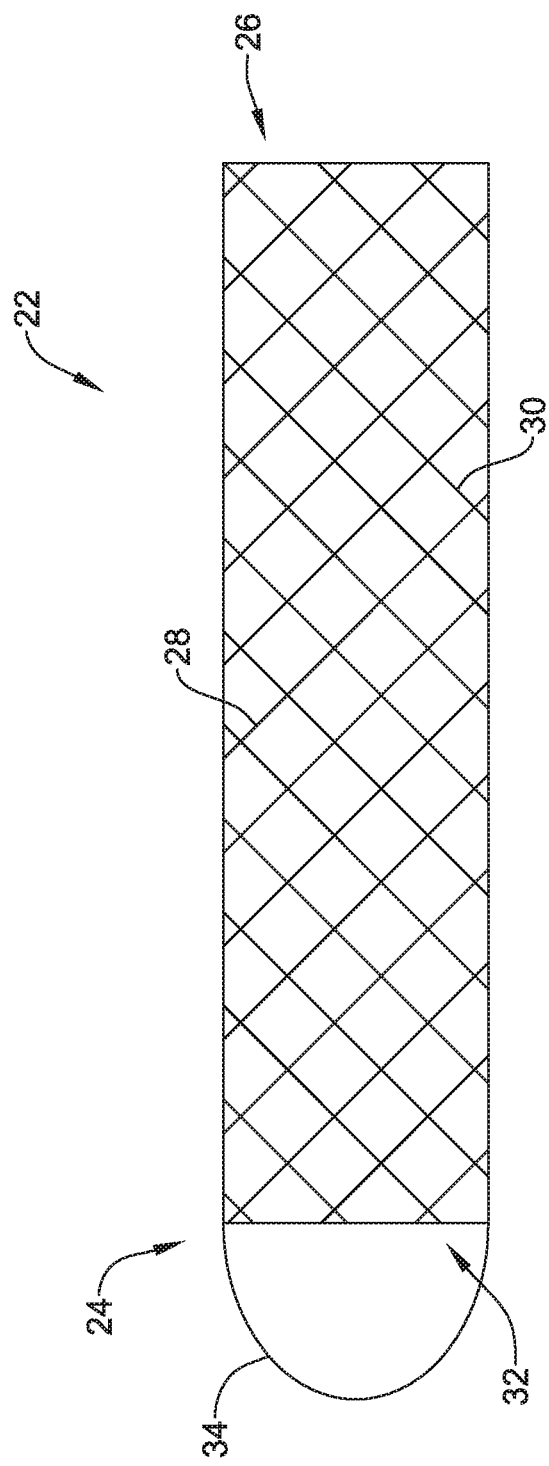
FIG. 2 is a perspective view of a tubular support structure useful as part of the stent of FIG. 1.

FIG. 2 is a perspective view of a tubular support structure 22. While the tubular support structure 22 is illustrated as a braided support structure, it will be appreciated that the tubular support structure 22 may take a variety of forms, including but not limited to a braided support structure, a knit support structure, a laser cut slotted tube, a polymeric structure, and the like. The tubular support structure 22 has a proximal end 24 and a distal end 26. In some embodiments, the tubular support structure 22 may be considered as forming part of the stent 10 (FIG. 1), optionally in combination with a polymeric covering or sleeve. In the illustrated embodiment, the tubular support structure 22 includes a plurality of windings 28 extending circumferentially in a first direction about the tubular support structure 22 and a plurality of windings 30 extending circumferentially in a second, different, direction about the tubular support structure 22. The plurality of windings 28 and 30, in combination, form the tubular support structure 22. A lumen 32 extends through an interior of the tubular support structure 22. The tubular support structure 22 may include a retrieval loop 34 that can be used for retrieving the tubular support structure 22, or a stent including the tubular support structure 22, once implanted. It will be appreciated that a braided stent will decrease in diameter when a pulling force is applied to an end of the braided stent. In other embodiments, the tubular support structure of the stent 10 may include a laser cut tubular member, a coiled tubular structure, a knitted tubular member, or other woven tubular structure, for example.

Figure 3:
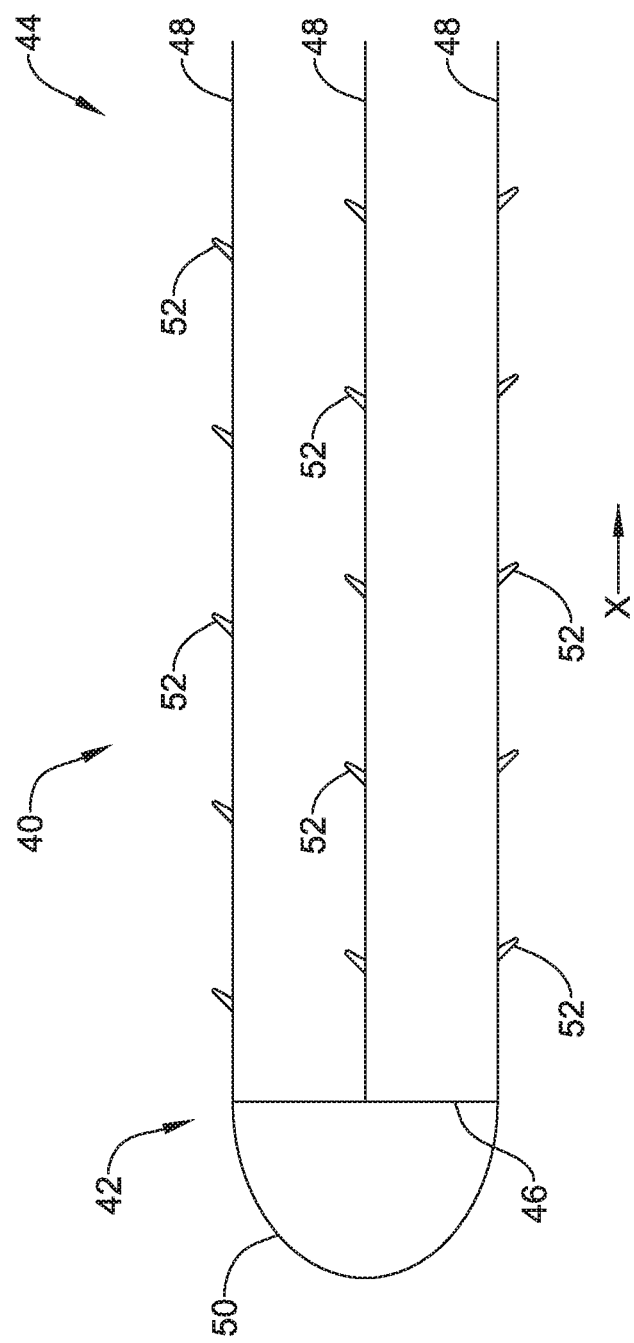
FIG. 3 is a perspective view of a retractable anchor system useable with the stent of FIG. 1, shown in a deployed configuration.
Figure 4:
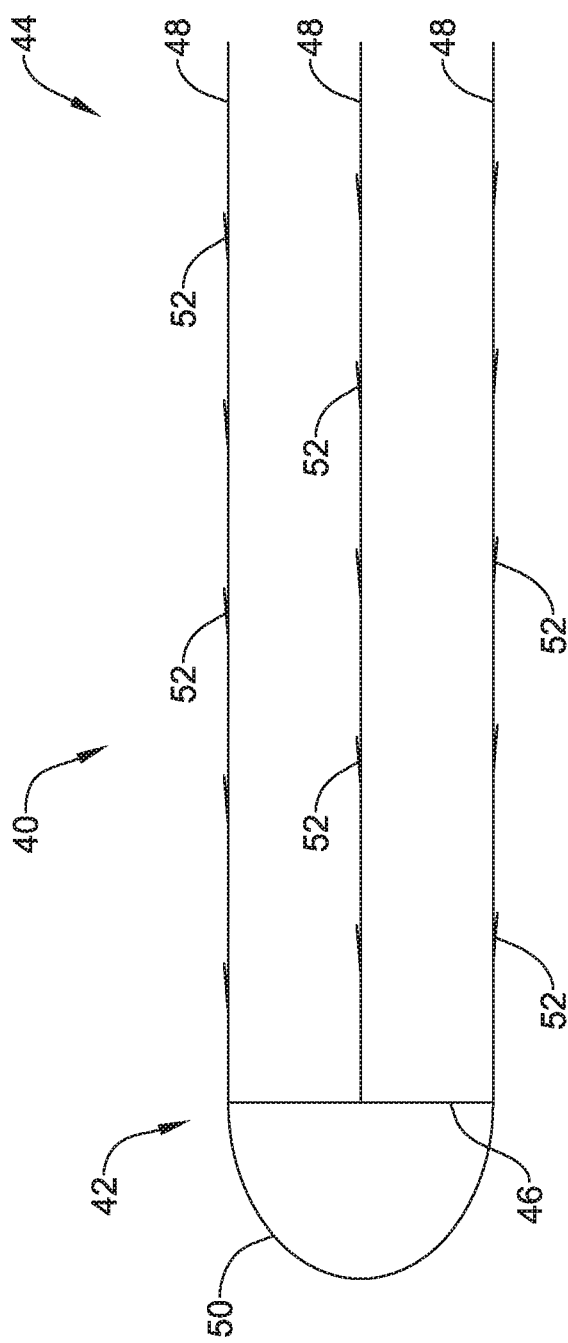
FIG. 4 is a perspective view of the retractable anchor system of FIG. 3, shown in a delivery configuration.

In some embodiments, the stent 10 may include, and thus be delivered and deployed with, structure that is configured to help hold the stent 10 in place once the stent 10 has been delivered and deployed at a desired target location within a patient. In some embodiments, it is contemplated that the stent 10 may be delivered separately from structure that is configured to help hold the stent 10 in place. FIGS. 3 and 4 are perspective views of a retractable anchor system 40. While shown alone, it will be appreciated that the retractable anchor system 40 may be used in combination with the tubular support structure 22 and thus may be secured to the tubular support structure 22 prior to deployment. In some embodiments, the retractable anchor system 40 may be sized and otherwise configured to be used with any desired stent 10, such as a pre-existing stent construction or a newly developed stent construction. The retractable anchor system 40 has a proximal end 42 and a distal end 44. The retractable anchor system 40 includes a ring 46 and one or more frame members 48 extending distally from the ring 46. A retraction member 50 is secured relative to the ring 46, and permits the retractable anchor system 40 to be grabbed for retrieval. Each of the one or more frame members 48 include a plurality of retractable anchors 52.

In FIG. 3, the plurality of retractable anchors 52 are shown in a deployed configuration, in which the retractable anchors 52 are pointed in a first direction labeled as X such that the retractable anchor system 40 resists movement in the first direction X labeled as X. In some cases, all or virtually all of the plurality of retractable anchors 52 point in the first direction labeled as X. In some cases, some of the plurality of retractable anchors 52 may point in the first direction labeled as X while others of the plurality of retractable anchors 52 point in a second direction opposite the first direction. In some embodiments, the retractable anchors 52 may form an angle relative to their corresponding frame member 48 that is in the range of about 5 degrees to about 90 degrees, or 5 degrees to 90 degrees, or about 30 degrees to about 60 degrees, or 30 degrees to 60 degrees, about 40 degrees to about 75 degrees, or 40 degrees to 75 degrees, about 45 degrees to about 90 degrees, or 45 degrees to 90 degrees, or about 30 degrees to about 90 degrees, or 30 degrees to 90 degrees, when in the deployed configuration.

In FIG. 4, the plurality of retractable anchors 52 are shown in a compressed configuration in which the retractable anchors 52 are deflected radially inward toward and closer to the particular frame member 48 to which they are attached. The angle of the retractable anchors 52 relative to the frame member 48 in the compressed configuration may be less than their angle in the deployed configuration. In some embodiments, the retractable anchors 52 may form an angle relative to their corresponding frame member 48 in the compressed configuration that is in the range of about 0 degrees to about 30 degrees, or 0 degrees to 30 degrees, about 0 degrees to about 20 degrees, or 0 degrees to 20 degrees, about 0 degrees to about 10 degrees, or 0 degrees to 10 degrees, or about 0 degrees to about 5 degrees, or 0 degrees to 5 degrees, for example. In some instances, FIG. 4 may be considered as representing a delivery configuration, in which a delivery sheath (not illustrated) is deployed over the retractable anchor system 40 to hold the retractable anchors 52 in the illustrated configuration for delivery. As will be discussed, FIG. 4 may also be considered as representing a retrieval configuration.

In some embodiments, the retractable anchors 52 may be formed separately from the frame members 48 and subsequently attached using any suitable attachment technique, including but not limited to welding, soldering or the use of adhesives. In some cases, at least some of the retractable anchors 52 may be hingedly secured to the frame members 48, or otherwise movably secured to the frame members 48. In some embodiments, the retractable anchors 52 may be integrally formed with the frame members 48. For example, a frame member 48 may be formed from a length of wire extending axially for a distance, then a short section of wire can double up on itself to form a retractable anchor, then extend axially for another distance, then doubled up on itself, and so on. In either case, it will be appreciated that while a total of three frame members 48 are illustrated, the retractable anchor system 40 may include a single frame member 48, two frame members 48, or four or more frame members 48, if desired. In some embodiments, each frame member 48 is a unitary component, all formed of a single material. In some cases, each frame member 48 may be a composite construction, formed of two or more distinct structures, each formed of one or more distinct materials. While the retractable anchors 52 are illustrated as being uniformly spaced, in some cases the inter-anchor spacing may vary. In some cases, for example, the spacing between adjacent retractable anchors 52 may vary in accordance with the relative position on the retractable anchor system 40. The inter-anchor spacing may increase or decrease in a step-wise or continuous fashion in accordance with the specific anatomical structures expected to be encountered upon deployment. The length of each retractable anchor 52 may be the same, or may vary. Accordingly, in some instances, a first region of the stent 10 may include retractable anchors 52 having a first configuration (e.g., a first length, angle, spacing, etc.) while a second region of the stent 10 may include retractable anchors 52 having a second, different configuration (e.g., a second length, angle, spacing, etc.).

In some embodiments, some or all of the retractable anchor system 40 may be formed of a shape memory material. In particular, in some cases the retractable anchors 52 may be formed of a shape memory material, and may be biased to the deployed configuration shown for example in FIG. 3. Once a delivery sheath is retracted, the retractable anchors 52 are free to return to a radially extended configuration radially outward of the outer surface of the tubular support structure 22 so that they can penetrate tissue and help prevent migration. In some cases, at least some of the retractable anchors 52 are configured to be atraumatic, and thus may push against tissue without penetrating the tissue, or with less penetration. In some instances, the retractable anchor system 40, or at least some of the retractable anchors 52, may be formed of a bioabsorbable material such that after a predetermined amount of time, the retractable anchor system 40 or portions thereof may dissolve in place. For example, in some cases, the stent 10 may be non-absorbable, and the retractable anchor system 40 may be bioabsorbable. As a result, the stent 10 may be held in place for a predetermined amount of time, then permitted to be removed or migrate as the retractable anchor system 40 dissolves. In other instances, the stent 10 and the retractable anchor system 40 may both be formed of a bioabsorbable material.

Figure 5:
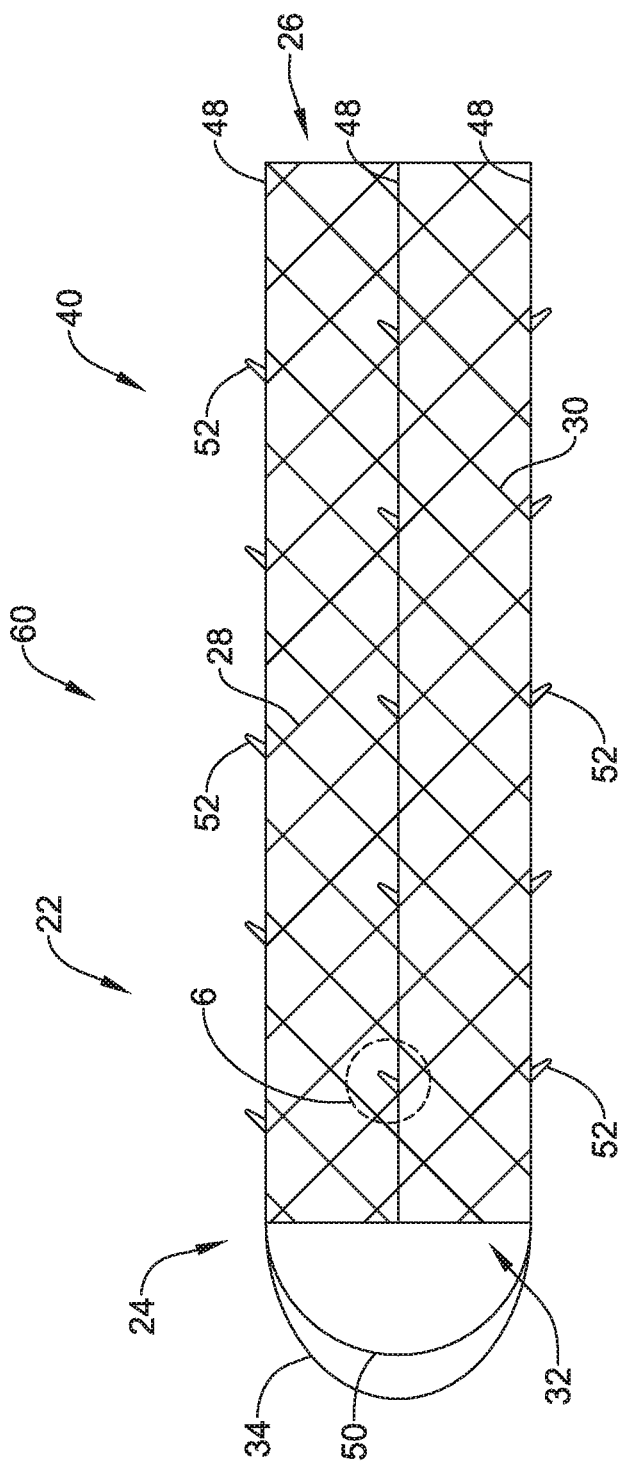
FIG. 5 is a perspective view of the retractable anchor system of FIG. 3 in combination with the stent of FIG. 1.

FIG. 5 provides a perspective view of an assembly 60 that includes the tubular support structure 22 in combination with the retractable anchor system 40. In some embodiments, the retractable anchor system may be loosely attached to the tubular support structure 22. For example, one or more of the frame members 48 of the retractable anchor system 40 may be woven into the tubular support structure 22 such that the retractable anchor system 40 remains disposed relative to the tubular support structure 22 while the frame member 48 may move axially relative to the tubular support structure 22. In other instances, the frame members 48 may extend along a radially inward surface of the support structure 22, for example.

Figure 6:
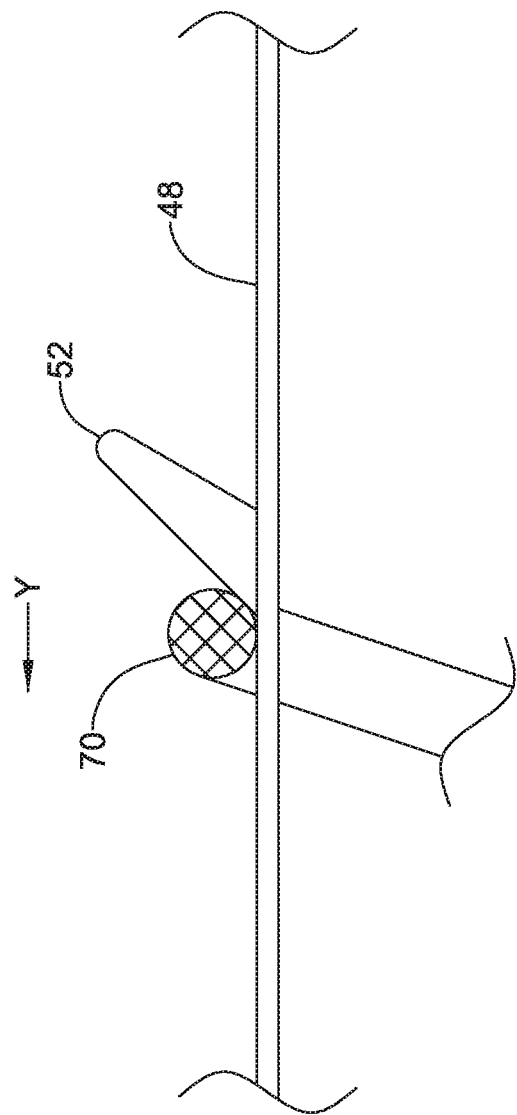
FIG. 6 is an enlarged view of a portion of FIG. 5, with a retractable anchor in a deployed configuration.

In some cases, small relative movement between the tubular support structure 22 and the retractable anchor system 40 may help move the retractable anchor system 40 into a configuration in which the retractable anchors 52 are compressed against the tubular support structure 22, such as was shown in FIG. 4. For example, FIG. 6 is an enlarged view of a portion of FIG. 5, illustrating a relationship between a frame member 48, a single retractable anchor 52 formed as part of the frame member 48 or otherwise secured to the frame member 48 and a winding 70 of the tubular support structure 22. It will be appreciated that the winding 70 may generically represent one of the first plurality of windings 28 or one of the second plurality of windings 30.

Figure 7:
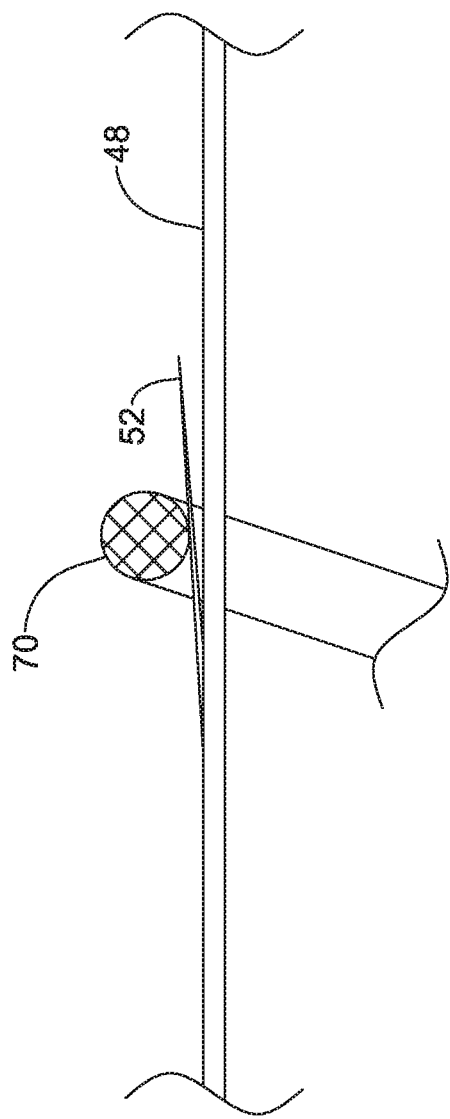
FIG. 7 illustrates the portion of FIG. 5 as seen in FIG. 6, with the retractable anchor system moved relative to the stent to move the retractable anchor into a retrieval configuration.

In FIG. 6, it can be seen that the winding 70 is disposed proximate the retractable anchor 52. By providing a proximal force on the retractable anchor system 40, such as by pulling on the retraction member 50 (FIG. 3), the retractable anchor system 40, and hence the frame member 48 and retractable anchor 52, moves in the direction labeled as Y. As can be seen in FIG. 7, this relative axial movement causes the winding 70 to push the retractable anchor 52 radially inward towards the frame member 48 and thus into a retracted configuration for retrieval. The stent 10 may be retrieved by holding a pulling force on the retraction member 50 while also providing a pulling force on the retrieval loop 34 (FIG. 3). In some embodiments, the stent 10 and the retractable anchor system 40 may both be withdrawn by pulling on the retraction member 50. Upon application of an initial pulling force on the retraction member 50, the retractable anchor system 40 will move proximally relative to the stent 10, moving the retractable anchors 52 into their retrieval configuration. Further application of a pulling force will then cause the stent 10 to move proximally with the retractable anchor system 40. In some instances, the stent 10 may not include the retrieval loop 34. In other embodiments, a strut or other structure of the support structure 22 may engage the retractable anchor 52 to push the retractable anchor 52 radially inward towards the frame member 48.

Figure 8:
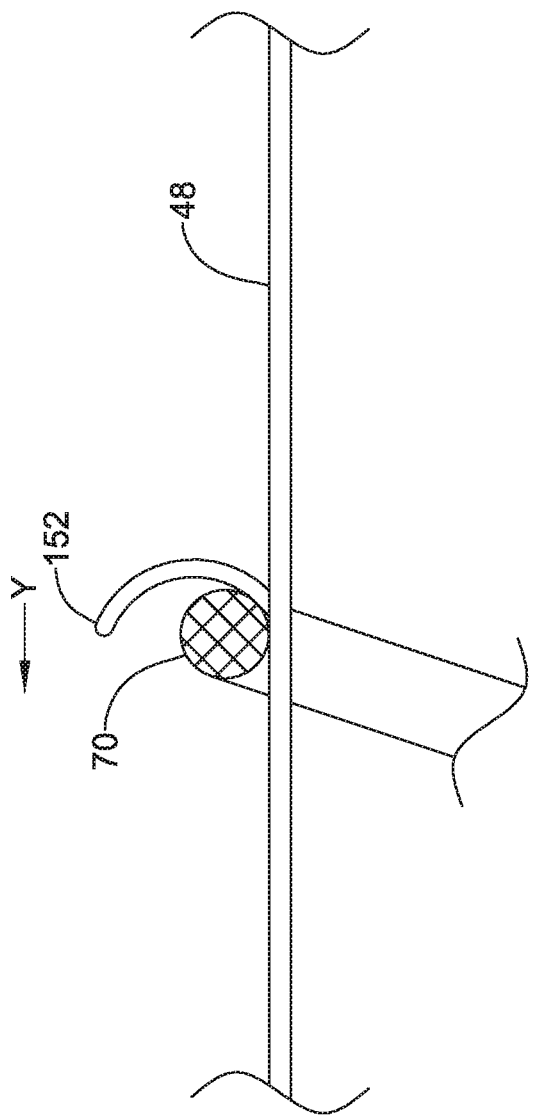
FIG. 8 is an alternate enlarged view of a portion of FIG. 5, with a loop-like retractable anchor in a deployed configuration.
Figure 9:
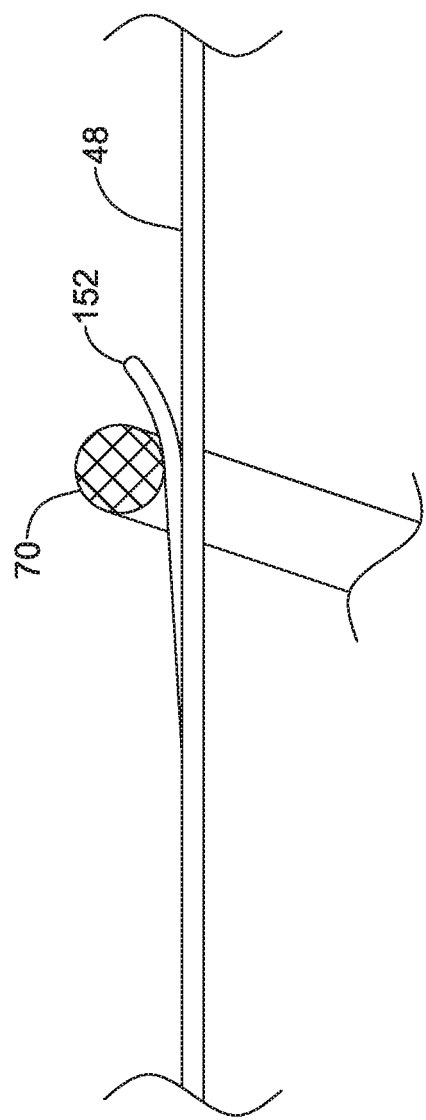
FIG. 9 illustrates the alternate portion of FIG. 5 as seen in FIG. 8, with the retractable anchor system moved relative to the stent to move the loop-style retractable anchor into a retrieval configuration.

In some embodiments, the retractable anchors 52 may have a more loop-like shape or arcuate curvature. In FIG. 8, it can be seen that the winding 70 is disposed proximate the retractable anchor 152. By providing a proximal force on the retractable anchor system 40, such as by pulling on the retraction member 50 (FIG. 3), the retractable anchor system 40, and hence the frame member 48 and retractable anchor 152, moves in the direction labeled as Y. As can be seen in FIG. 9, this relative axial movement causes the winding 70 to push the retractable anchor 152 radially inward towards the frame member 48 and thus into a retracted configuration for retrieval. Accordingly, the retractable anchor 152 may be deflected from a curved, deployed configuration (shown in FIG. 8) to a more straightened, retracted configuration (shown in FIG. 9). In some instances, the radius of curvature of the arcuate shaped retractable anchor 152 may be increased from a first radius of curvature in the deployed configuration to a second radius of curvature, greater than the first radius of curvature, in the retracted configuration. The stent 10 may be retrieved by holding a pulling force on the retraction member 50 while also providing a pulling force on the retrieval loop 34 (FIG. 3), as discussed above with respect to FIGS. 6 and 7.

Figure 10:
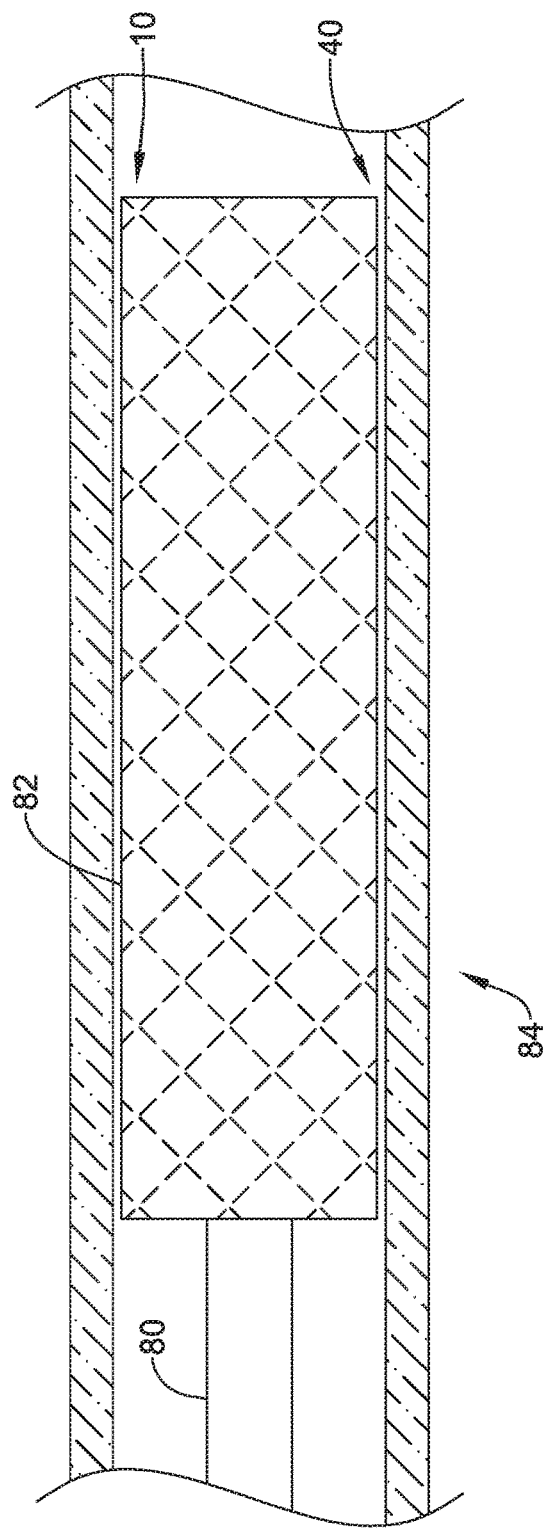
FIGS. 10 and 11 illustrate deployment of the combination shown in FIG. 5.
Figure 11:
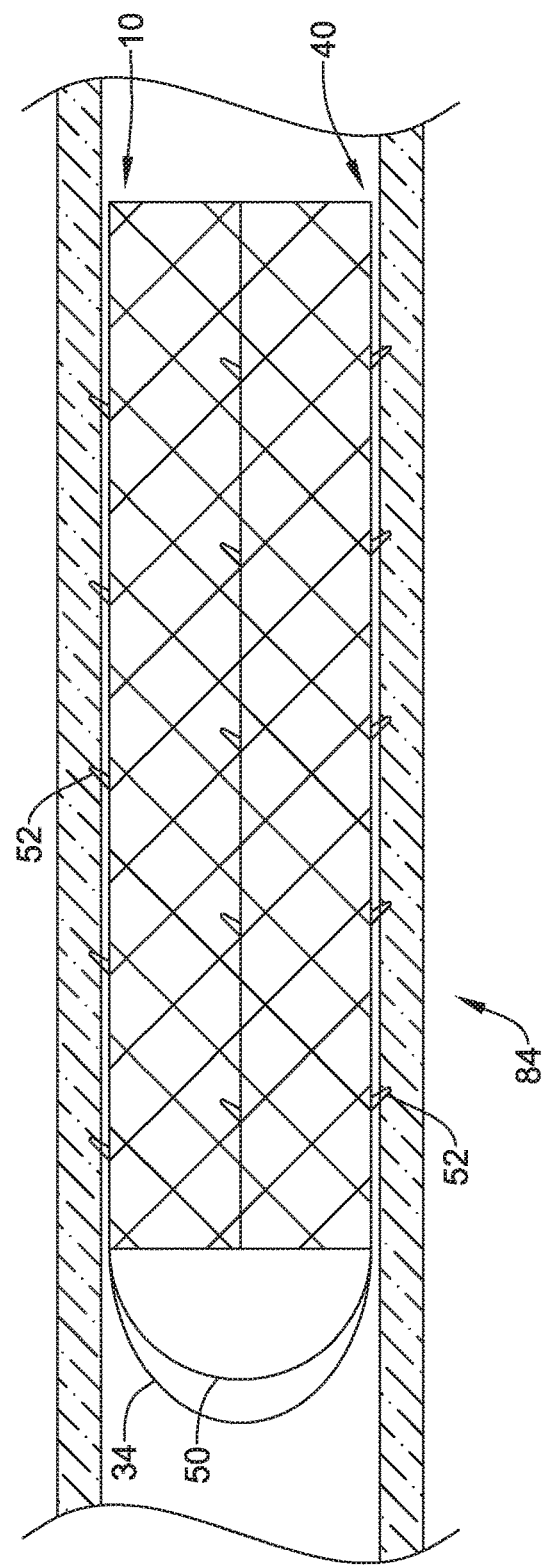

FIGS. 10 and 11 provide an illustrative but non-limiting example of deploying the stent 10. In FIG. 10, the stent 10, in combination with the retractable anchor system 40, are seen loaded on a delivery catheter 80. A delivery sheath 82 is disposed over the stent 10 and the retractable anchor system 40. The delivery catheter 80 is shown within a target location 84 within a patient. In some embodiments, the target location 84 may be within the patient's esophagus, but this is not required. By retracting the delivery sheath 82, the stent 10 is able to expand to a deployed configuration and the retractable anchor system 40 is also able to move into its deployed configuration in which the retractable anchors 52 extend radially away from the frame members 48 and radially outward of the outer surface of the tubular support structure 22 to penetrate into the tissue at the target location 84. In some embodiments, the retractable anchor system 40 may be configured to permit a small amount of axial movement relative to the stent 10. As discussed above with respect to FIGS. 6 and 7, this relative axial movement may be useful in transitioning the retractable anchor system 40 from the deployed configuration to a retrieval configuration for retrieval of the stent 10.

It will be appreciated that a variety of different materials may be used in forming the stent 10. In some embodiments, a polymeric covering or coating, if included, may include any suitable polymeric material, including biocompatible materials such as polyurethane or silicone. Other suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

The stent 10, the tubular support structure 22 and the retractable anchor system 40 may be formed of any suitable desired material, such as a biocompatible material including biostable, bioabsorbable, biodegradable or bioerodible materials. For instance, the stent 10, the tubular support structure 22 and the retractable anchor system 40 may be formed of a metallic material. Some suitable metallic materials include, but are not necessarily limited to, stainless steel, tantalum, tungsten, nickel-titanium alloys such as those possessing shape memory properties commonly referred to as nitinol, nickel-chromium alloys, nickel-chromium-iron alloys, cobalt-chromium-nickel alloys, or other suitable metals, or combinations or alloys thereof.

In some embodiments, the stent 10, the tubular support structure 22 and the retractable anchor system 40 may include one or more metals. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In some embodiments, the stent 10 and/or the retractable anchor system 40 may include one or more coatings, which may be applied to the stent 10, to the retractable anchor system 40 or to the combination. Coatings may include any desired biocompatible coatings, including but not limited to elutable drugs. The terms "therapeutic agents," "drugs," "bioactive agents," "pharmaceuticals," "pharmaceutically active agents", and other related terms may be used interchangeably herein and include genetic therapeutic agents, non-genetic therapeutic agents, and cells. Therapeutic agents may be used singly or in combination. A wide range of therapeutic agent loadings can be used in conjunction with the devices of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth.

Some specific beneficial agents include anti-thrombotic agents, anti-proliferative agents, anti-inflammatory agents, anti-migratory agents, agents affecting extracellular matrix production and organization, antineoplastic agents, antimitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

More specific drugs or therapeutic agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, and Serca 2 gene/protein, resiquimod, imiquimod (as well as other imidazoquinoline immune response modifiers), human apolioproteins (e.g., AI, AII, AIII, AIV, AV, etc.), vascular endothelial growth factors (e.g., VEGF-2), as well as derivatives of the forgoing, among many others.

Numerous additional therapeutic agents useful for the practice of the present invention may be selected from those described in paragraphs [0040] to [0046] of commonly assigned U.S. Patent Application Pub. No. 2003/0236514, the entire disclosure of which is hereby incorporated by reference.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A stent comprising:
    a tubular support structure extending from a distal end to a proximal end, the tubular support structure including an inner surface and an outer surface; and
    a retractable anchor system disposed relative to the tubular support structure such that the retractable anchor system is movable axially relative to the tubular support structure, the retractable anchor system including a frame member and a plurality of retractable anchors secured to the frame member;
    wherein the plurality of retractable anchors are biased to a deployed configuration in which the plurality of retractable anchors extend radially outward from the outer surface of the tubular support structure but are radially inwardly compressible into a delivery configuration by contact with the tubular support structure;
    wherein the frame member is woven into the tubular support structure.

2. The stent of claim 1, wherein the retractable anchor system comprises a shape memory material.

3. The stent of claim 1, wherein the plurality of retractable anchors are configured such that when the stent is implanted, the plurality of retractable anchors are pointed in a first direction to resist movement of the stent in the first direction.

4. The stent of claim 1, wherein the retractable anchor system includes a retraction member at a proximal end of the retractable anchor system, such that a proximal force applied to the retraction member causes the retractable anchor system to move proximally relative to the tubular support structure such that at least some of the retractable anchors are deflected radially inwardly via contact with a portion of the tubular support structure for subsequent removal of the stent.

5. The stent of claim 1, wherein the retractable anchor system further comprises one or more additional frame members, each of which include a plurality of retractable anchors.

6. The stent of claim 5, wherein each of the frame members are joined to a ring disposed at an end of the retractable anchor system.

7. The stent of claim 1, wherein a portion of the retractable anchor system is disposed adjacent the inner surface of the tubular support structure.

8. The stent of claim 1, wherein the retractable anchors are disposed adjacent the outer surface of the tubular support structure.

9. The stent of claim 1, wherein the tubular support structure is self-expanding.

10. A stent comprising:
    a tubular support structure extending from a distal end to a proximal end, the tubular support structure including an inner surface and an outer surface; and
    a retractable anchor system disposed relative to the tubular support structure, the retractable anchor system including a frame member and a plurality of retractable anchors secured to the frame member;
    wherein the plurality of retractable anchors are biased to a deployed configuration in which the plurality of retractable anchors extend radially outward from the outer surface of the tubular support structure but are radially inwardly compressible into a delivery configuration;
    wherein the plurality of retractable anchors are movable between the delivery configuration and the deployed configuration via axial movement of the retractable anchor system relative to the tubular support structure;

wherein the frame member is woven into the tubular support structure.

11. The stent of claim 10, wherein the plurality of retractable anchors are configured such that when the stent is implanted, the plurality of retractable anchors are pointed in a first direction to resist movement of the stent in the first direction.

12. The stent of claim 10, wherein the retractable anchor system includes a retraction member at a proximal end thereof, such that a proximal force applied to the retraction member causes the retractable anchor system to move proximally relative to the tubular support structure such that at least some of the retractable anchors are deflected radially inwardly via contact with a portion of the tubular support structure for subsequent removal of the stent.

13. A stent comprising:
  a braided support structure extending from a distal end to a proximal end of the stent, the braided support structure including an inner surface and an outer surface;
  a polymeric covering disposed on the braided support structure; and
  a retractable anchor system including:
    a plurality of frame members extending along the braided support structure; and
    a plurality of retractable anchors secured to each of the plurality of frame members;
    wherein the retractable anchor system is movable axially relative to the braided support structure;
    wherein the plurality of retractable anchors are biased to a position in which the plurality of retractable anchors extend radially outward from the outer surface of the braided support structure.

14. The stent of claim 13, wherein the braided support structure is self-expanding.

15. The stent of claim 13, wherein the retractable anchor system comprises a shape memory material.

16. The stent of claim 13, wherein the plurality of retractable anchors are configured such that when the stent is implanted, the plurality of retractable anchors are pointed in a first direction to resist downward movement of the stent in the first direction.

17. The stent of claim 13, wherein the retractable anchor system includes a retraction member at a proximal end of the retractable anchor system, such that a proximal force applied to the retraction member causes the retractable anchor system to move proximally relative to the braided support structure such that at least some of the retractable anchors are deflected radially inwardly via contact with a portion of the braided support structure for subsequent removal of the stent.

* * * * *